(12) United States Patent
Plos et al.

(10) Patent No.: US 7,338,535 B2
(45) Date of Patent: Mar. 4, 2008

(54) PROCESS FOR RAPID DYEING AND RAPID DECOLORATION OF HUMAN KERATIN FIBRES WITH CERTAIN DIRECT DYES

(75) Inventors: Grégory Plos, Paris (FR); Frédéric Guerin, Paris (FR)

(73) Assignee: L'Oreal S.A., Paris (FR)

( * ) Notice: Subject to any disclaimer, the term of this patent is extended or adjusted under 35 U.S.C. 154(b) by 79 days.

(21) Appl. No.: 10/688,999

(22) Filed: Oct. 21, 2003

(65) Prior Publication Data

US 2004/0078906 A1 Apr. 29, 2004

Related U.S. Application Data

(60) Provisional application No. 60/423,996, filed on Nov. 6, 2002.

(30) Foreign Application Priority Data

Oct. 21, 2002 (FR) .................................. 02 13097

(51) Int. Cl.
*A61K 7/13* (2006.01)
(52) U.S. Cl. ........................ 8/405; 8/426; 8/428; 8/454; 8/462
(58) Field of Classification Search .................... 8/405, 8/426, 428, 435, 454, 462
See application file for complete search history.

(56) References Cited

U.S. PATENT DOCUMENTS

| 5,474,578 | A | * | 12/1995 | Chan et al. | ............ | 8/431 |
| 5,931,973 | A | * | 8/1999 | Malle et al. | ............ | 8/431 |
| 6,171,347 | B1 | * | 1/2001 | Kunz et al. | ............ | 8/407 |
| 6,231,622 | B1 | * | 5/2001 | Chassot et al. | ............ | 8/405 |
| 6,541,032 | B1 | | 4/2003 | Medelnick et al. | | |
| 2002/0139957 | A1 | | 10/2002 | Matsuo et al. | | |
| 2003/0159221 | A1 | | 8/2003 | Lang | | |
| 2004/0143910 | A1 | * | 7/2004 | Said et al. | ............ | 8/405 |

FOREIGN PATENT DOCUMENTS

| EP | 0 547 790 A1 | 6/1993 |
| EP | 0 796 850 | 9/1997 |
| FR | 2 070 879 | 9/1971 |
| FR | 2 818 536 | 6/2002 |
| JP | A-5-221837 | 8/1993 |
| JP | A-2001-163729 | 6/2001 |
| JP | A-2001-294519 | 10/2001 |
| JP | A-2002-265338 | 9/2002 |
| WO | WO 95/15144 | 6/1995 |
| WO | WO 01/66068 | 9/2001 |
| WO | WO 02/100367 | 12/2002 |

OTHER PUBLICATIONS

English language Derwent abstract of JP-A-5-221837.
English language Derwent abstract of JP-A-2001-294519.
Automatic English translation from the Japanese Patent Office of JP-A-2001-294519.
English language Derwent Abstract of FR 2 070 879, Sep. 17, 1971.
English language Derwent Abstract of FR 2 818 536, Jun. 28, 2002.
English language Derwent abstract of JP-A-5-221837 (1993).
English language Derwent abstract of JP-A-2001-294519 (2001).
Automatic English translation from the Japanese Patent Office of JP-A-2001-294519 (2001).

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

Disclosed herein is a rapid dyeing process for human keratin fibers, such as hair, comprising applying to the keratin fibers at least one dye composition comprising, in a medium suitable for dyeing, at least one direct dye chosen from arylmethane dyes, cationic azo dyes, methine dyes, azomethine dyes and azine dyes; maintaining the composition in contact with the keratin fibers for a leave-in time of less than 5 minutes; and rinsing the treated keratin fibers; wherein the resulting coloration has, according to the CIELAB notation, an L* value of less than 40 and/or a C* value of greater than 20, such as greater than 25, when the composition is applied to natural hair containing 90% white hairs at a temperature of 27° C.±5° C. for a period of 4 minutes, for a bath ratio of 10. Further disclosed herein is a process for stripping the keratin fibers colored with the direct dye, comprising applying an oxidizing or reducing treatment in a time period of less than 5 minutes.

35 Claims, No Drawings

PROCESS FOR RAPID DYEING AND RAPID DECOLORATION OF HUMAN KERATIN FIBRES WITH CERTAIN DIRECT DYES

This application claims benefit of U.S. Provisional Application No. 60/423,996, filed Nov. 6, 2002.

Disclosed herein are a process for rapid dyeing of human keratin fibers, such as hair, with at least one direct dye, and a process of decoloration of the human keratin fibers from the direct dye.

In modern, active life, many people wish to change their hair color, but do not go through with it due to lack of time. The dye products currently available on the market do not make it possible to dye the hair significantly in a very short leave-in time, since at least between 20 and 30 minutes are generally needed to achieve an appreciable dyeing result.

Some people also wish to change their hair color very frequently, which can be difficult to achieve for technical reasons, since they need to go through a stripping step under oxidizing or reducing conditions, which step is generally slow.

The present inventors have surprisingly discovered that it is possible to obtain strong colorations very quickly within an interval of less than 5 minutes, even on unsensitized hair, by using at least one direct dye chosen from arylmethane dyes, cationic azo dyes, methine dyes, azomethine dyes, and azine dyes.

The inventors have found that strong colorations can thus be obtained very quickly, even on unsensitized hair. The inventors have further found that these direct dyes can be eliminated very quickly and the hair can regain its original color, without causing any problem for subsequent colorations, by applying an oxidizing or reducing treatment, also within a very short time of less than 5 minutes.

Disclosed herein is a process for dyeing human keratin fibers, such as the hair, using at least one of these direct dyes, wherein this process can have a very short leave-in time of less than 5 minutes.

Other subjects of the invention will become apparent on reading the description and the examples that follow.

The dyeing process disclosed herein comprises applying to human keratin fibers, such as the hair, at least one dye composition comprising, in a medium suitable for dyeing, at least one direct dye chosen from arylmethane dyes, cationic azo dyes, methine dyes, azomethine dyes, and azine dyes; keeping the at least one dye composition in contact with the human keratin fibers for a leave-in time of less than 5 minutes; and rinsing the treated human keratin fibers; wherein the resulting coloration has, according to the CIELAB notation, an $L^*$ value of less than 40 and/or a $C^*$ value of greater than 20, when the at least one dye composition is applied to natural hair containing 90% white hairs, at a temperature of 27° C.±5° C. for a period of 4 minutes for a bath ratio of 10. As disclosed herein, the term "bath ratio" means the ratio of the weight of the dye composition to the weight of the human keratin fibers, such as the hair.

In one embodiment, the at least one direct dye is chosen from those which can give, at 0.5% by weight relative to the total weight of the at least one dye composition, an $L^*$ value of less than 40 and/or a $C^*$ value of greater than 25 for a leave-in time of 1 minute on natural hair containing 90% white hairs, at room temperature (27° C.±5° C.) for a bath ratio of 10.

The CIELAB notation defines a colorimetric space in which each color is defined by three parameters ($L^*$, $a^*$ and $b^*$):

the parameter $L^*$ reflects the lightness of the color, the value $L^*$ being equal to 0 for black and equal to 100 for absolute white. The higher the value of $L^*$, the less strong the coloration, the parameter $a^*$ corresponds to the axis of the green/red antagonistic pair, the parameter $b^*$ corresponds to the axis of the blue/yellow antagonistic pair, the value of the parameter $C^*$ or chromaticity index is equal to $\sqrt{(a^{*2}+b^{*2})}$.

The arylmethane dyes, which can be used herein, are, for example, chosen from the compounds corresponding to formulae (I), (II), (III) and (IV) below:

triaminotriphenylmethane compounds

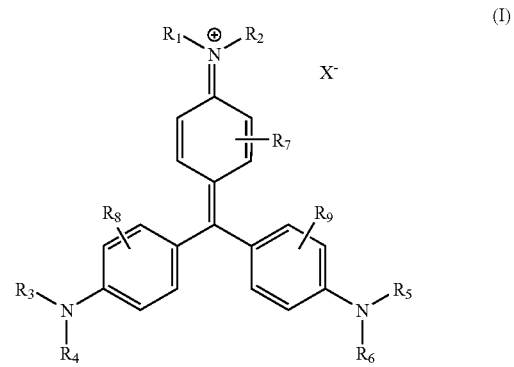

(I)

wherein:

$R_1$, $R_2$, $R_3$, $R_4$, $R_5$ and $R_6$, which may be identical or different, are each chosen from a hydrogen atom, $C_1$-$C_4$ alkyl groups such as methyl and ethyl groups, $C_1$-$C_4$ mono- and polyhydroxyalkyl groups such as a β-hydroxyethyl group, a phenyl group, and a benzyl group, and $R_7$, $R_8$ and $R_9$, which may be identical or different, are each chosen from a hydrogen atom, halogen atoms such as chlorine, and $C_1$-$C_4$ alkyl groups such as methyl and ethyl groups.

Examples that may be mentioned include Basic Red 9 (Basic Fuchsin C. I. 42500), Basic Violet 1 (Methyl Violet 2B C.I.42535), Basic Violet 2 (New Fuchsin C.I. 42520) and Opal Blue SS.

diaminotriphenylmethane compounds

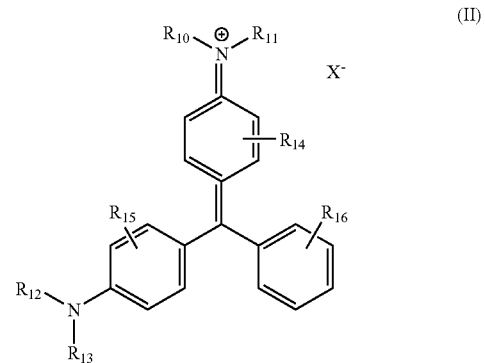

(II)

wherein:

$R_{10}$, $R_{11}$, $R_{12}$ and $R_{13}$, which may be identical or different, are each chosen from a hydrogen atom, $C_1$-$C_4$ alkyl groups such as methyl and ethyl groups, and $C_1$-$C_4$ mono- and polyhydroxyalkyl groups such as a β-hydroxyethyl group, $R_{14}$ and $R_{15}$, which may be identical or different, are each chosen from a hydrogen atom, $C_1$-$C_4$ alkyl groups such as methyl and ethyl groups, and $C_1$-$C_4$ mono- and polyhydroxyalkyl groups such as a β-hydroxyethyl group, and $R_{16}$ is chosen from a hydrogen atom, halogen atoms such as chlorine, $C_1$-$C_4$ alkyl groups such as methyl and ethyl groups, and $C_1$-$C_4$ mono- and polyhydroxyalkyl groups such as a β-hydroxyethyl group.

Examples that may be mentioned include Basic Blue 1 (C.I.42025), Basic Green 1 (Brilliant Green 1 C.I.42040), Basic Green 4 (Malachite Green Oxalate C.I.42000) and Basic Blue 5 (Brilliant Glacier Blue C.I.42140).

triaminonaphthyldiphenylmethane compounds

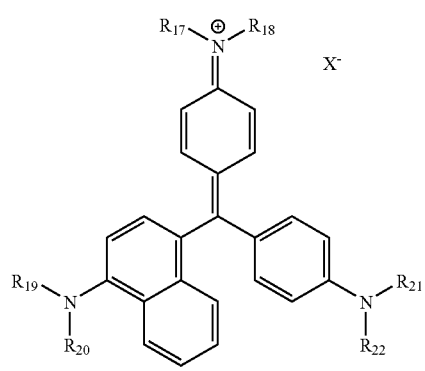

(III)

wherein:

$R_{17}$, $R_{18}$, $R_{21}$ and $R_{22}$, which may be identical or different, are each chosen from $C_1$-$C_4$ alkyl groups such as methyl and ethyl groups, and $C_1$-$C_4$ mono- and polyhydroxyalkyl groups such as a β-hydroxyethyl group, and $R_{19}$ and $R_{20}$, which may be identical or different, are each chosen from a hydrogen atom, $C_1$-$C_4$ alkyl groups such as an ethyl group, $C_1$-$C_4$ mono- and polyhydroxyalkyl groups such as a β-hydroxyethyl group, a phenyl group, a benzyl group, and a toluyl group.

Examples that may be mentioned include Basic Blue 11 (Victoria Blue R C.I.44040), Basic Blue 15 (Bleu de nuit C.I.44085) and Basic Blue 26 (Victoria blue B C.I.44045).

monoaminotriphenylmethane compounds

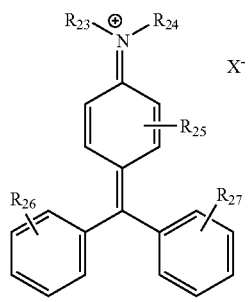

(IV)

wherein:

$R_{23}$ and $R_{24}$, which may be identical or different, are each chosen from a hydrogen atom, $C_1$-$C_4$ alkyl groups such as methyl and ethyl groups, $C_1$-$C_4$ mono- and polyhydroxyalkyl groups, and a benzyl group, and $R_{25}$, $R_{26}$ and $R_{27}$, which may be identical or different, are each chosen from a hydrogen atom, halogen atoms such as chlorine, and $C_1$-$C_4$ alkyl groups such as methyl and ethyl groups.

An example that may be mentioned is fuchsonimine hydrochloride (CAS# 84215-84-9).

The cationic azo dyes that may be used herein are chosen from the monocationic and polycationic azo dyes of the following formula (V):

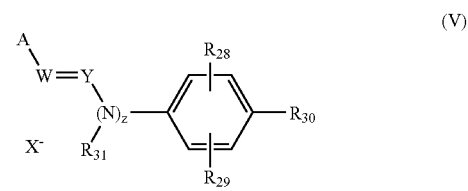

(V)

wherein:

A is of one of the following formulae:

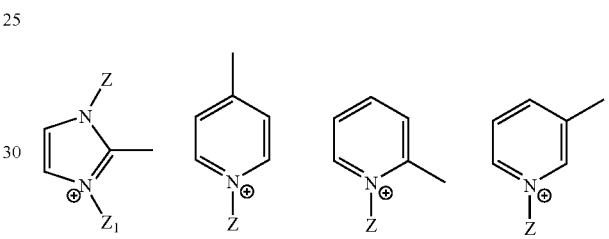

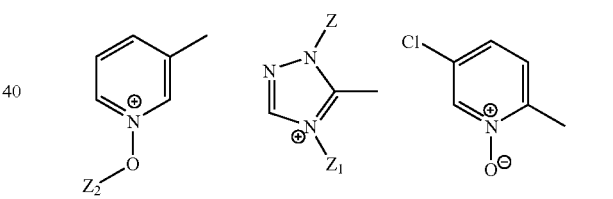

W and Y, which may be identical or different, are each chosen from a nitrogen atom and a CH group, Z, $Z_1$ and $Z_2$, which may be identical or different, are each chosen from $C_1$-$C_4$ alkyl groups, such as a methyl group, $R_{28}$ and $R_{29}$, which may be identical or different, are each chosen from a hydrogen atom, halogen atoms, linear and branched $C_1$-$C_4$ alkyl groups, linear and branched $C_1$-$C_4$ alkoxy groups, and a phenol group making it possible to form a naphthalene sequence with the adjacent phenyl group, z is an integer that may be 0 or 1, wherein when z=0, either Y or $R_{31}$ connects directly to the benzene ring, $R_{30}$ is chosen from a hydrogen atom, linear and branched $C_1$-$C_4$ alkoxy groups, groups $NR_{32}R_{33}$, wherein $R_{32}$ and $R_{33}$, which may be identical or different, are each chosen from a hydrogen atom, linear and branched $C_1$-$C_4$ alkyl groups, a toluyl group, $C_1$-$C_4$ mono- and polyhydroxyalkyl groups such as a hydroxyethyl group, a —$CH_2SO_3Na$ group, and a benzyl group, or forms a heterocycle with the adjacent nitrogen atom and at least one carbon atom of the benzene ring, $R_{31}$ is chosen from a hydrogen atom and linear and branched $C_1$-$C_4$ alkyl groups, or forms a heterocycle with the adjacent nitrogen atom and at least one carbon atom of the benzene ring.

An example that may be mentioned is Basic Red 46 (C.I. 110825).

The methine and azomethine dyes derived from an indolinium or benzothiazolinium ring, which may be used herein, are chosen from those of formulae (VI), (VII) and (VIII) below:

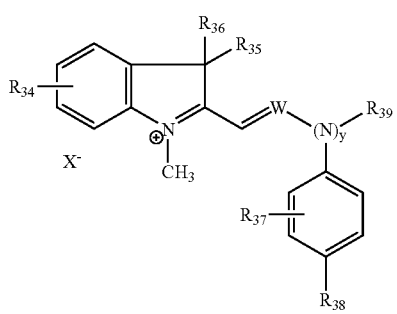

(VI)

wherein:

$R_{34}$, $R_{35}$ and $R_{36}$, which may be identical or different, are each chosen from a hydrogen atom and $C_1$-$C_4$ alkyl groups such as a methyl group, W is chosen from a nitrogen atom and a CH group, y is an integer that may be 0 or 1, wherein when y=0, either W or $R_{39}$ connects directly to the benzene ring, $R_{37}$ is chosen from a hydrogen atom, $C_1$-$C_4$ alkyl groups such as a methyl group, and $C_1$-$C_4$ alkoxy groups such as a methoxy group, $R_{38}$ is chosen from a hydrogen atom, a methoxy group, groups $NR_{40}R_{41}$ wherein $R_{40}$ and $R_{41}$, which may be identical or different, are each chosen from $C_1$-$C_4$ alkyl groups such as methyl, ethyl and propyl groups optionally substituted with at least one entity chosen from a chlorine atom and a cyano group, $R_{39}$ is chosen from a hydrogen atom and $C_1$-$C_4$ alkyl groups, such as a methyl group, or forms a heterocycle with the adjacent nitrogen atom and the at least one carbon atom of the adjacent benzene ring.

Examples that may be mentioned include Basic Red 13 (C.I. 48015), Basic Red 14 (C.I. 48016), Basic Violet 7 (C.I. 48020), Basic Yellow 23 (C.I. 48100) and Basic Yellow 28 (C.I. 48054).

Similarly, the methine dye Basic Orange 21 (C.I.48035) of formula (VII) may be used herein.

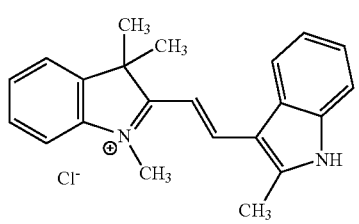

(VII)

It is lso possible to use the carbocyanin of formula (VIII):

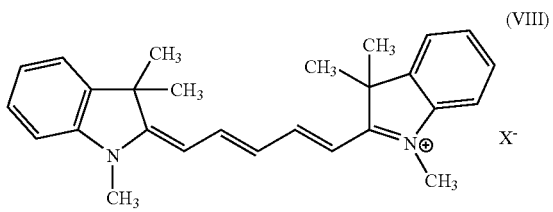

(VIII)

Benzothiazole derivatives of formula (IX) may also be used herein:

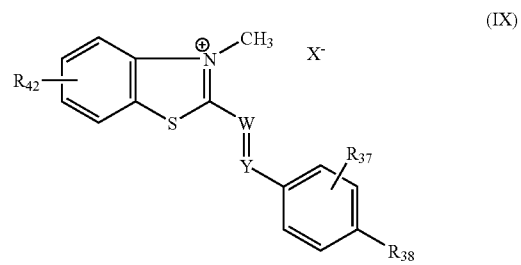

(IX)

wherein:

$R_{42}$ is chosen from a hydrogen atom, $C_1$-$C_4$ alkyl groups such as methyl and ethyl groups, and $C_1$-$C_4$ alkoxy groups such as a methoxy group, $R_{37}$ and $R_{38}$ have the same meaning as in formula (VI), W and Y, which may be identical or different, are each chosen from a nitrogen atom and a CH group.

An example that may be mentioned is Basic Blue 41 (C.I. 11105).

The azine dyes, comprising the phenazines (formula X), the azophenazines (formula XI), the thiazines (formula XII) and the oxazines (formula XIII) that may be used herein are given below:

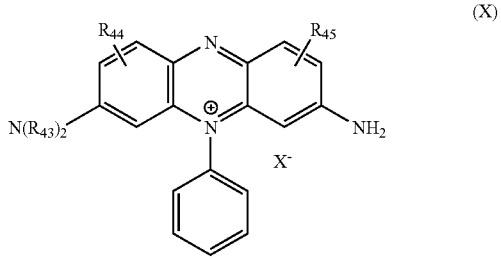

(X)

wherein $R_{43}$, $R_{44}$ and $R_{45}$, which may be identical or different, are each chosen from a hydrogen atom and $C_1$-$C_4$ alkyl groups such as methyl and ethyl groups.

An example that may be mentioned is Methylene Violet 3RAX (C.I.50206)

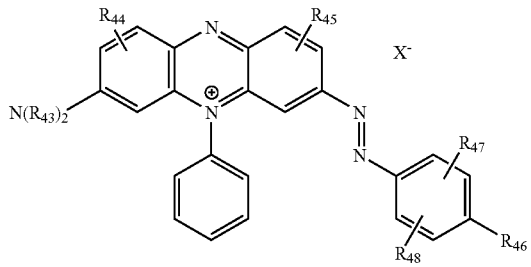

(XI)

wherein:

$R_{43}$, $R_{44}$ and $R_{45}$ have the same meaning as in formula (X), $R_{46}$ is chosen from a hydrogen atom, a hydroxyl group and an amino group, $R_{47}$ and $R_{48}$, which may be identical or different, are each chosen from a hydrogen atom, a hydroxyl group and a phenyl group making it possible to form a naphthalene sequence with the adjacent phenyl group.

Examples that may be mentioned include Basic Blue 16 (C.I.12210), Basic Black 2 (C.I.11815) and Janus Green B (C.I.11050).

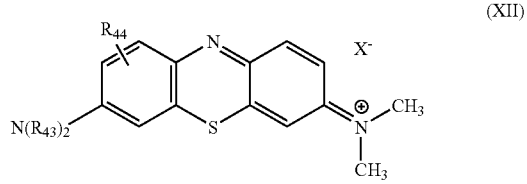

(XII)

wherein $R_{43}$ and $R_{44}$ have the same meaning as in formula (X).

Examples that may be mentioned include Basic Blue 17 (C.I.52040) and Basic Blue 9 (C.I. 52015).

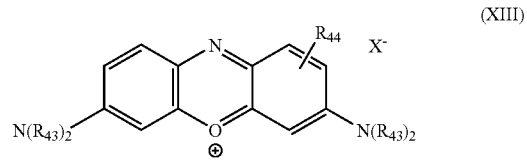

(XIII)

wherein $R_{43}$ and $R_{44}$ have the same meaning as in formula (X).

An example that may be mentioned is Basic Blue 3 (C.I. 51004).

In each of the above formulae (I)-(XIII), $X^-$ is an anion chosen from ions derived from halogen atoms, such as a chlorine atom, and $HSO_4^-$, methosulphate, benzoate and acetate ions.

The dyes Basic Red 22, Basic Blue 7 and Basic Violet 14 are not among the direct dyes that may be used herein.

The concentration of the at least one direct dye ranges, for example, from 0.001% to 10% by weight, such as from 0.05% to 5% by weight, relative to the total weight of the composition. This concentration depends on the strength of coloration desired to be obtained.

The application temperature ranges, for example, from room temperature to 80° C., such as from room temperature to 60° C. In one embodiment, the hair is dyed at a temperature of 27° C.±5° C.

The application time ranges, for example, from 30 seconds to less than 5 minutes, such as from 1 minute to 3 minutes, and further such as from 1 minute to 2 minutes.

The hair is then rinsed with water.

The pH for the dye composition ranges, for example, from 2 to 11, such as from 3 to 11.

The dye compositions disclosed herein can be applied to any type of hair, such as hair that has undergone a bleaching treatment. The compositions disclosed herein may be in the form of foam (aerosol), cream, gel, lotion or shampoo.

The dye compositions disclosed herein can comprise at least one cosmetic adjuvant chosen from conventional cosmetic adjuvants, such as anionic, cationic, nonionic and amphoteric surfactants, thickening polymers, conditioners (cationic polymers, cations, silicones, etc.), solvents, alkaline agents, and acidic agents.

The oxidizing stripping operation can be performed by any oxidizing treatment, such as by applying hydrogen peroxide or compounds capable of producing hydrogen peroxide by hydrolysis, such as urea peroxide and persalts, for example, perborates, percarbonates and persulphates. In one embodiment, hydrogen peroxide is used.

The more alkaline the pH of the stripping composition, the more efficient is this oxidizing stripping operation.

Stripping in a reducing medium, which is, for example, acidic, may also be used. As reducing agents that may be used, mention may be made of sulphites, hydrosulphites and sulphinates.

The stripping operation disclosed herein may be characterized by its speed, of less than 5 minutes for the envisaged structures, irrespective of the nature of the hair. The stripping does not result in any damage to or lightening of the hair, because of the short leave-in time.

After stripping, the hair may be recolored without loss of the dyeing power.

The examples that follow are intended to illustrate the invention without being limiting in nature.

EXAMPLE 1

A direct dye was introduced at a concentration of 0.5% by weight relative to the total weight of the composition into the support below:

| Component | Concentration* |
|---|---|
| Benzyl alcohol | 10% |
| Polyethylene glycol (8 EO) | 12% |
| Hydroxyethylcellulose MW 720 000 sold by the company Aqualon | 1.5% |
| Direct dye** | 0.5% |
| pH | spontaneous |
| Distilled water | qs 100% |

*wherein the concentration is weight percentage relative to the total weight of the composition.
**The direct dye was chosen from:
triarylmethane compounds: Basic Blue 1, Basic Blue 11, Basic Green 1, Basic Violet 1, Basic Violet 2, and Basic Violet 4, cationic azo compounds: Basic Red 46,

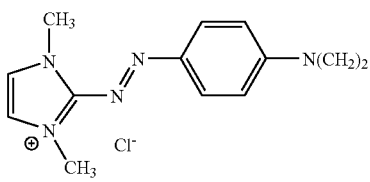

Basic Red 51

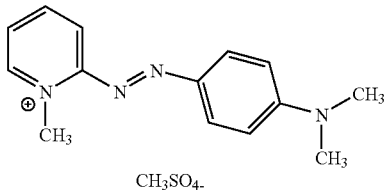

Colorant B cyanin methine compounds: Basic Red 14, Basic Yellow 13, Basic Yellow 23, and Basic Yellow 28.

These compositions were each applied at a temperature of 27° C.±5° C. to 1-gram locks of natural hair containing 90% white hairs, with a bath ratio of 10, for 1 minute. The locks were then rinsed with clear water, shampooed and dried. After drying, the locks were read in a Minolta CM 2002 spectrocolorimeter (10% angle, specular components excluded, illuminant D65) in the CIE L*a*b* system. The L*a*b* values of the control lock are: L*=58.16; a*=0.86; and b*=10.5.

The colorimetric results are given below:

| Dye | L* | a* | b* | C* |
|---|---|---|---|---|
| Basic Blue 1 | 37.02 | −23.22 | −8.75 | 24.81 |
| Basic Blue 11 | 27.97 | 8.74 | −23.64 | 25.20 |
| Basic Green 1 | 38.75 | −29.20 | 0.20 | 29.20 |
| Basic Violet 1 | 27.41 | 15.34 | −19.27 | 24.63 |
| Basic Violet 2 | 31.20 | 23.34 | −3.56 | 23.61 |
| Basic Violet 4 | 27.78 | 13.99 | −27.83 | 31.15 |
| Basic Red 51 | 32.29 | 33.16 | 2.74 | 33.27 |
| Colorant B | 26.22 | 23.72 | −15.87 | 28.54 |
| Basic Red 46 | 36.84 | 34.25 | 3.65 | 34.46 |
| Basic Red 14 | 43.34 | 34.23 | 3.56 | 34.41 |
| Basic Yellow 13 | 55.83 | −4.85 | 41.21 | 41.45 |
| Basic Yellow 23 | 55.48 | −4.84 | 45.42 | 45.68 |
| Basic Yellow 28 | 50.24 | 13.62 | 41.00 | 43.20 |

These calorimetric results show that the very short leave-in time on the hair allows colorations of very good strength to be obtained by using the compositions disclosed herein.

EXAMPLE 2

The locks colored in Example 1 with Basic Green 1, Basic Violet 1, Basic Violet 2, Basic Violet 4, Basic Red 14, Basic Yellow 13 and Basic Yellow 23 were completely stripped in less than 5 minutes with 20-volumes aqueous hydrogen peroxide solution adjusted to pH 11 with sodium hydroxide.

What is claimed is:

1. A rapid dyeing process for human keratin fibers, comprising
applying to the human keratin fibers at least one dye composition comprising, in a medium suitable for dyeing, at least one direct dye chosen from the following dyes:
arylmethane dyes, and
methine and azomethine dyes, chosen from
the triaminotriphenylmethane compounds of formula (I):

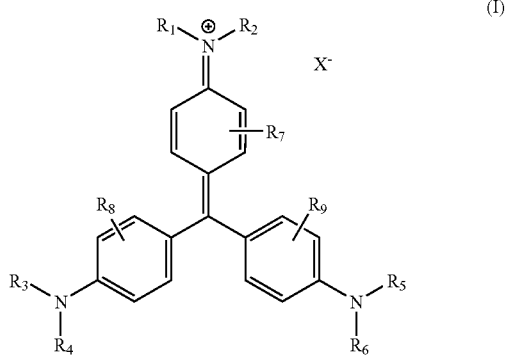

wherein:
$R_1$, $R_2$, $R_3$, $R_4$, $R_5$ and $R_6$, which may be identical or different, are each chosen from a hydrogen atom, $C_1$-$C_4$ alkyl groups, $C_1$-$C_4$ mono- and polyhydroxyalkyl groups, a phenyl group and a benzyl group, and
$R_7$, $R_8$ and $R_9$, which may be identical or different, are each chosen from a hydrogen atom, halogen atoms, and $C_1$-$C_4$ alkyl groups;
the diaminotriphenylmethane compounds of formula (II)

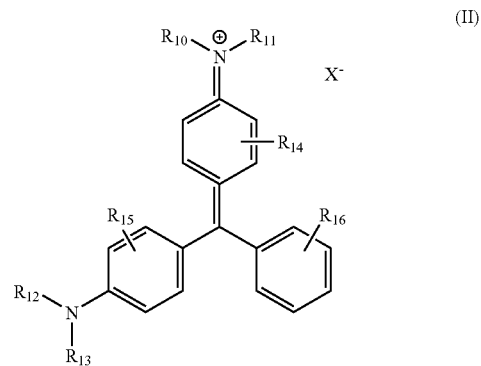

wherein:
$R_{10}$, $R_{11}$, $R_{12}$ and $R_{13}$, which may be identical or different, are each chosen from a hydrogen atom, $C_1$-$C_4$ alkyl groups, and $C_1$-$C_4$ mono- and polyhydroxyalkyl groups,
$R_{14}$ and $R_{15}$, which may be identical or different, are each chosen from a hydrogen atom, $C_1$-$C_4$ alkyl groups, and $C_1$-$C_4$ mono- and polyhydroxyalkyl groups, and
$R_{16}$ is chosen from a hydrogen atom, halogen atoms, $C_1$-$C_4$ alkyl groups, and $C_1$-$C_4$ mono- and polyhydroxyalkyl groups;
the triaminonaphthyldiphenylmethane compounds of formula (III)

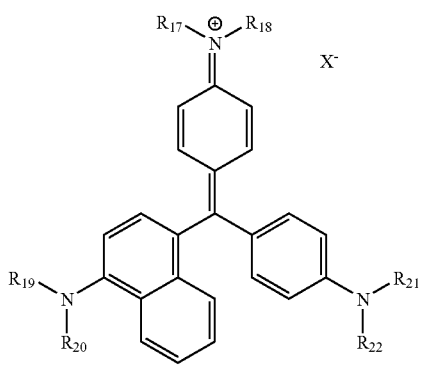

wherein:

$R_{17}$, $R_{18}$, $R_{21}$ and $R_{22}$, which may be identical or different, are each chosen from $C_1$-$C_4$ alkyl groups and $C_1$-$C_4$ mono- and polyhydroxyalkyl groups, and $R_{19}$ and $R_{20}$, which may be identical or different, are each chosen from a hydrogen atom, $C_1$-$C_4$ alkyl groups, $C_1$-$C_4$ mono- and polyhydroxyalkyl groups, a phenyl group, a benzyl group, and a toluyl group;

the monoaminotriphenylmethane compounds of formula (IV)

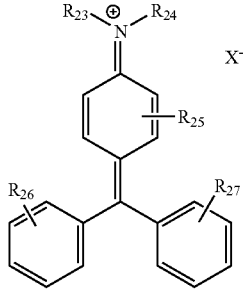

wherein:

$R_{23}$ and $R_{24}$, which may be identical or different, are each chosen from a hydrogen atom, $C_1$-$C_4$ alkyl groups, $C_1$-$C_4$ mono- and polyhydroxyalkyl groups, and a benzyl group, and $R_{25}$, $R_{26}$ and $R_{27}$, which may be identical or different, are each chosen from a hydrogen atom, halogen atoms, and $C_1$-$C_4$ alkyl groups; and the methine and azomethine dyes of formula (VI):

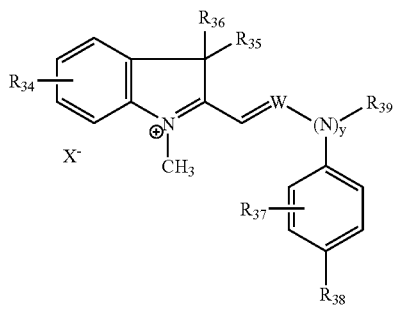

wherein:

$R_{34}$, $R_{35}$ and $R_{36}$, which may be identical or different, are each chosen from a hydrogen atom and $C_1$-$C_4$ alkyl groups, W is a CH group, y is the integer 0, wherein either W or $R_{39}$ connects directly to the benzene ring, $R_{37}$ is chosen from a hydrogen atom, $C_1$-$C_4$ alkyl groups, and $C_1$-$C_4$ alkoxy groups, $R_{38}$ is chosen from a hydrogen atom, a methoxy group, groups $NR_{40}R_{41}$ wherein R40 and R41, which may be identical or different, are each chosen from $C_1$-$C_4$ alkyl groups optionally substituted with at least one entity chosen from a chlorine atom and a cyano group, and $R_{39}$ is chosen from a hydrogen atom and $C_1$-$C_4$ alkyl groups, or forms a heterocycle with the adjacent nitrogen atom and at least one carbon atom of the adjacent benzene ring, in each of the above formulae (I)-(IV) and (VI), X is an anion chosen from anions derived from halogen atoms, and $HSO_4^-$, methosulphate, benzoate and acetate ions maintaining the at least one dye composition in contact with said keratin fibers for a leave-in time of less than 5 minutes; and rinsing the treated keratin fibers, wherein the resulting coloration has, according to the CIELAB notation, an L* value of less than 40 and a C* value of greater than 20, when the at least one dye composition is applied to natural hair containing 90% white hairs, at a temperature of 27° C.±5° C. for a period of 4 minutes, for a bath ratio of 10.

2. The rapid dyeing process according to claim 1, wherein the human keratin fibers are hair.

3. The rapid dyeing process according to claim 1, wherein the coloration has, according to the CIELAB notation, an L* value of less than 40 and a C* value of greater than 25, when the at least one dye composition is applied to natural hair containing 90% white hairs, at a temperature of 27° C.±5° C. for a period of 4 minutes, for a bath ratio of 10.

4. The rapid dyeing process according to claim 1, wherein in defining $R_7$, $R_8$, and $R_9$ in the formula (I), at least one of the halogen atoms is a chlorine atom.

5. The rapid dyeing process according to claim 1, wherein in defining $R_1$, $R_2$, $R_3$, $R_4$, $R_5$, $R_6$, $R_7$, $R_8$, or $R_9$ in the formula (I), at least one of the $C_1$-$C_4$ alkyl groups is chosen from methyl and ethyl groups.

6. The rapid dyeing process according to claim 1, wherein in defining $R_1$, $R_2$, $R_3$, $R_4$, $R_5$ and $R_6$ in the formula (I), the $C_1$-$C_4$ mono- and polyhydroxyalkyl groups are chosen from a β-hydroxyethyl group.

7. The rapid dyeing process according to claim 1, wherein in defining $R_{10}$, $R_{11}$, $R_{12}$, $R_{13}$, $R_{14}$, $R_{15}$, or $R_{16}$ in the formula (II), at least one of the $C_1$-$C_4$ alkyl groups is chosen from methyl and ethyl groups.

8. The rapid dyeing process according to claim 1, wherein in defining $R_{10}$, $R_{11}$, $R_{12}$, $R_{13}$, $R_{14}$, $R_{15}$, or $R_{16}$ in the formula (II), at least one of the $C_1$-$C_4$ mono- and polyhydroxyalkyl groups is a β-hydroxyethyl group.

9. The rapid dyeing process according to claim 1, wherein in defining $R_{16}$ in the formula (II), the halogen atom is a chlorine atom.

10. The rapid dyeing process according to claim 1, wherein in defining $R_{17}$, $R_{18}$, $R_{21}$, and $R_{22}$ in the formula (III), the $C_1$-$C_4$ alkyl groups are chosen from methyl and ethyl groups.

11. The rapid dyeing process according to claim 1, wherein in defining $R_{17}$, $R_{18}$, $R_{19}$, $R_{20}$, $R_{21}$, or $R_{22}$ in the formula (III), at least one of the $C_1$-$C_4$ mono- and polyhydroxyalkyl groups is a β-hydroxyethyl group.

12. The rapid dyeing process according to claim 1, wherein in defining $R_{19}$ and $R_{20}$ in the formula (III), the $C_1$-$C_4$ alkyl groups are chosen from an ethyl group.

13. The rapid dyeing process according to claim 1, wherein in defining $R_{23}$, $R_{24}$, $R_{25}$, $R_{26}$, or $R_{27}$ in the formula (IV), at least one of the $C_1$-$C_4$ alkyl groups is chosen from methyl and ethyl groups.

14. The rapid dyeing process according to claim 1, wherein in defining $R_{25}$, $R_{26}$, and $R_{27}$ in the formula (IV), the halogen atom is a chlorine atom.

15. The rapid dyeing process according to claim 1, wherein in defining $R_{34}$, $R_{35}$, $R_{36}$, $R_{37}$, or $R_{39}$ in the formula (VI), at least one of the $C_1$-$C_4$ alkyl groups is chosen from a methyl group.

16. The rapid dyeing process according to claim 1, wherein in defining $R_{37}$ in the formula (VI), the $C_1$-$C_4$ alkoxy groups are chosen from a methoxy group.

17. The rapid dyeing process according to claim 1, wherein in defining $R_{40}$ and $R_{41}$ in $NR_{40}R_{41}$ for $R_{38}$ in the formula (VI), the C1-C4 alkyl groups are chosen from methyl, ethyl, and propyl groups.

18. The rapid dyeing process according to claim 1, wherein the leave-in time ranges from 1 to 3 minutes.

19. The rapid dyeing process according to claim 18, wherein the leave-in time ranges from 1 to 2 minutes.

20. The rapid dyeing process according to claim 1, wherein the concentration of the at least one direct dye ranges from 0.001% to 10% by weight, relative to the total weight of the composition.

21. The rapid dyeing process according to claim 20, wherein the concentration of the at least one direct dye ranges from 0.05% to 5% by weight, relative to the total weight of the composition.

22. The rapid dyeing process according to claim 1, wherein the pH of the composition ranges from 2 to 11.

23. The rapid dyeing process according to claim 22, wherein the pH of the composition ranges from 3 to 11.

24. The rapid dyeing process according to claim 1, wherein the application temperature ranges from room temperature to 80° C.

25. The rapid dyeing process according to claim 24, wherein the application temperature ranges from room temperature to 60° C.

26. The rapid dyeing process according to claim 25, wherein the application temperature is at 27° C.±5° C.

27. The rapid dyeing process according to claim 1, wherein the at least one dye composition further comprises at least one adjuvant chosen from anionic, cationic, nonionic and amphoteric surfactants, thickening polymers, conditioners, solvents, alkaline agents, and acidic agents.

28. A rapid stripping process for human keratin fibers, comprising applying to dyed human keratin fibers at least one compound chosen from oxidizing agents and reducing agents with a leave-in time of less than 5 minutes, wherein the dyed human keratin fibers are dyed by a rapid dyeing process, comprising
applying to said keratin fibers at least one dye composition comprising, in a medium suitable for dyeing, at least one direct dye chosen from the following dyes:
arylmethane dyes,
cationic azo dyes,
methine and azomethine dyes, and
azine dyes,
maintaining the at least one dye composition in contact with said keratin fibers for a leave-in time of less than 5 minutes; and
rinsing the treated keratin fibers,
wherein the resulting coloration has, according to the CIELAB notation, an L* value of less than 40 and /or a C* value of greater than 20, when the at least one dye composition is applied to natural hair containing 90% white hairs, at a temperature of 27° C.±5° C. for a period of 4 minutes, for a bath ratio of 10.

29. The rapid stripping process according to claim 28, wherein the human keratin fibers are hair.

30. The rapid stripping process according to claim 28, wherein the at least one direct dye is chosen from Basic Blue 1, Basic Blue 5, Basic Green 1, Basic Green 4, Basic Red 9, Basic Violet 1, Basic Violet 2, Basic Violet 3, Basic Violet 4, Hofmann's Violet, Opal Blue SS, Basic Orange 21, Basic Red 13, Basic Red 14, Basic Violet 16 and Basic Violet 7.

31. The rapid stripping process according to claim 28, wherein the stripping process uses at least one oxidizing agent and is performed at a basic pH.

32. The rapid stripping process according to claim 28, wherein the stripping process uses at least one reducing agent and is performed at an acidic pH.

33. The rapid stripping process according to claim 28, wherein the oxidizing agents are chosen from hydrogen peroxide, urea peroxide and persalts.

34. The rapid stripping process according to claim 33, wherein the persalts are chosen from perborates, percarbonates and persulphates.

35. The rapid stripping process according to claim 28, wherein the reducing agents are chosen from sulphites, hydrosulphites and sulphinates.

\* \* \* \* \*

UNITED STATES PATENT AND TRADEMARK OFFICE
CERTIFICATE OF CORRECTION

PATENT NO. : 7,338,535 B2
APPLICATION NO. : 10/688999
DATED : March 4, 2008
INVENTOR(S) : Grégory Plos and Frédéric Guerin It is certified that error appears in the above-identified patent and that said Letters Patent is hereby corrected as shown below:

On the title page, item (*), line 3, "79 days" should read --0 days--.

In Claim 1, col. 12, line 11, "R40 and R41" should read --$R_{40}$ and $R_{41}$--.

Signed and Sealed this

Sixth Day of January, 2009

JON W. DUDAS
*Director of the United States Patent and Trademark Office*